(12) United States Patent
Kern

(10) Patent No.: US 8,147,465 B2
(45) Date of Patent: Apr. 3, 2012

(54) DELIVERY NEEDLE APPARATUS WITH SLEEVE

(75) Inventor: Michael J. Kern, St. Louis Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 156 days.

(21) Appl. No.: 12/037,424

(22) Filed: Feb. 26, 2008

(65) Prior Publication Data

US 2009/0216202 A1 Aug. 27, 2009

(51) Int. Cl.
*A61M 5/32* (2006.01)
(52) U.S. Cl. ........................ 604/272; 604/264
(58) Field of Classification Search ............... 604/158, 604/164.01, 164.06, 164.07, 164.09, 164.11, 604/166.01, 170.03, 171, 264, 272
See application file for complete search history.

(56) References Cited

U.S. PATENT DOCUMENTS

| 3,459,188 | A | | 8/1969 | Roberts | |
|---|---|---|---|---|---|
| 3,680,562 | A | * | 8/1972 | Wittes et al. | 604/500 |
| 3,782,381 | A | | 1/1974 | Winnie | |
| 3,856,009 | A | | 12/1974 | Winnie | |
| 4,906,236 | A | * | 3/1990 | Alberts et al. | 604/198 |
| 5,478,328 | A | * | 12/1995 | Silverman et al. | 604/272 |
| 5,669,882 | A | | 9/1997 | Pyles | |
| 6,249,707 | B1 | | 6/2001 | Kohnen et al. | |
| 6,553,264 | B2 | | 4/2003 | Redko et al. | |
| 6,558,353 | B2 | | 5/2003 | Zohmann | |
| 2005/0090801 | A1 | | 4/2005 | Racz et al. | |

* cited by examiner

*Primary Examiner* — Bhisma Mehta
(74) *Attorney, Agent, or Firm* — Mueting, Raasch & Gebhardt, P.A.

(57) ABSTRACT

A delivery needle apparatus in which a sleeve is fitted over an exterior surface of a delivery needle and methods of manufacturing the same. An elongate medical device may be delivered through the interior of the delivery needle and out of an opening in the distal end of the delivery needle (i.e., the delivery opening). The sleeve may cover a proximal portion of the delivery opening and may align an elongate medical device during insertion and/or withdrawal through the delivery opening.

21 Claims, 4 Drawing Sheets

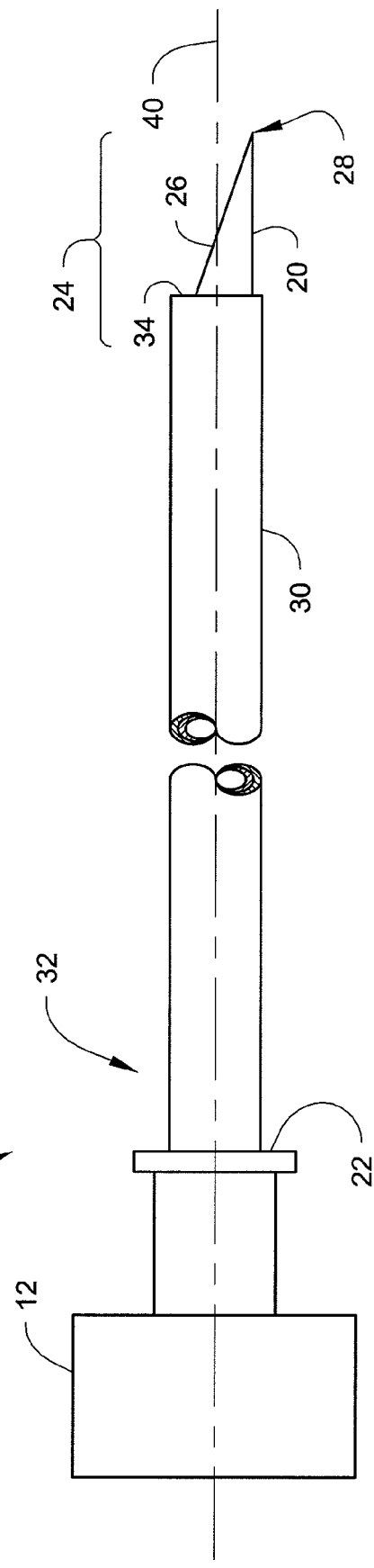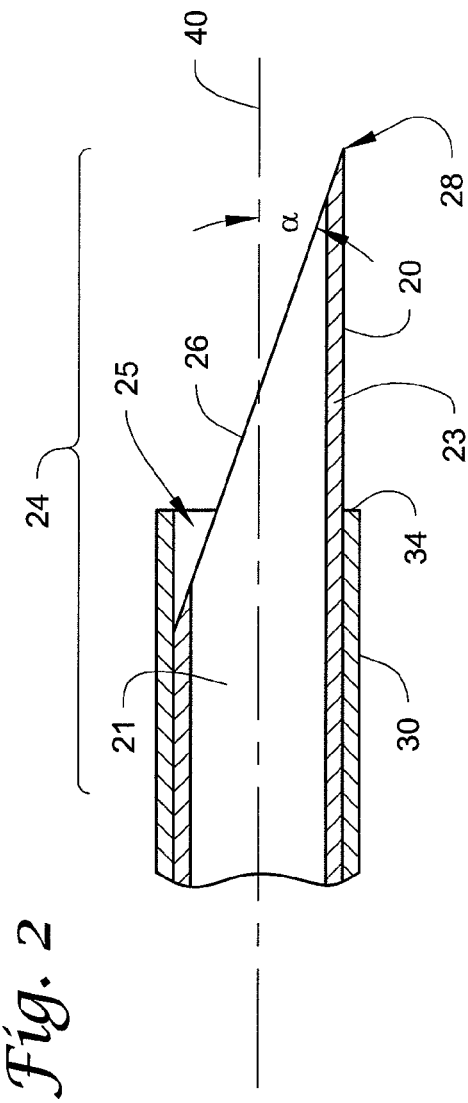
Fig. 1
Fig. 2

DELIVERY NEEDLE APPARATUS WITH SLEEVE

TECHNICAL FIELD

The present invention relates generally to a medical apparatus, and more, particularly, to a delivery needle apparatus with a sleeve for delivering elongate medical devices (e.g., a catheter, lead, etc.).

BACKGROUND

Treatment of diseases, ailments of the body, and surgical procedures often benefit from infusion of drugs, electrical signals, and/or other fluids. While such therapeutic treatment may be administered extracorporally, many patients benefit from the consistent and repeatable treatment provided by, e.g., catheters or neurostimulation leads. Such catheters or leads may be used in a variety of applications such as control of pain and/or spasticity.

Delivery needles may be used to deliver catheters, leads, etc. into a patient's body. As used herein, the term "elongate medical device" will be used to refer to catheters, leads, etc. that have elongate bodies amenable to delivery to a selected internal body location through a delivery needle. In particular, delivery needles may be used to position elongate medical devices into an epidural or intrathecal space of the spine, a selected location within the brain, or any other selected internal body location.

SUMMARY OF THE INVENTION

The present invention provides a delivery needle apparatus in which a sleeve is fitted over an exterior surface of a delivery needle. An elongate medical device may be delivered through the interior of the delivery needle and out of an opening in the distal end of the delivery needle (i.e., the delivery opening). The sleeve may cover a proximal portion of the delivery opening and may align an elongate medical device during insertion and/or withdrawal through the delivery opening.

In one aspect, the present invention may provide a delivery needle apparatus that includes a delivery needle body extending along a longitudinal axis from a proximal end to an insertion section, wherein the delivery needle body has a needle wall defining a lumen that extends into the insertion section, and wherein the delivery needle body further includes a delivery opening located within the insertion section, wherein the delivery opening is in fluid communication with the lumen; and a sleeve fixedly attached to the delivery needle body, wherein the sleeve is fitted over an exterior surface of the delivery needle body, and wherein at least a portion of the delivery opening is contained within the sleeve.

In some embodiments, the delivery needle apparatus may include a delivery opening that is formed through the needle wall within the insertion section, wherein the delivery opening has a longitudinal length measured along the longitudinal axis. Further, only a proximal portion of the delivery opening may be located within the sleeve such that a portion of the delivery opening is not contained within the sleeve, and wherein the delivery opening extends towards the proximal end of the needle body within the sleeve.

In other embodiments, the delivery opening of the delivery needle body may be located entirely within the sleeve such that an extension portion of the sleeve extends past the insertion section of the delivery needle body. The extension portion of the sleeve may be curved relative to the longitudinal axis of the delivery needle body.

In various embodiments, the delivery needle apparatus may include one or more of the following features: the sleeve may be fixedly attached to the needle body by friction between an inner surface of the sleeve and the exterior surface of the needle body; the sleeve may be fixedly attached to the needle body by adhesive located between an inner surface of the sleeve and the exterior surface of the needle body; the sleeve may extend proximally from the delivery opening to the proximal end of the needle body; the sleeve may have a proximal end located between the proximal end of the needle body and the delivery opening; the sleeve may include polymeric material; the sleeve may consist essentially of polymeric material; the needle body may include a metallic needle wall; etc.

In another aspect, the present invention may provide a delivery needle apparatus that includes a needle body extending along a longitudinal axis from a proximal end to an insertion section, wherein the needle body has a needle wall defining a lumen that extends into the insertion section; a delivery opening formed through the needle wall within the insertion section, wherein the opening has a longitudinal length measured along the longitudinal axis, and wherein the opening is in fluid communication with the lumen; and a sleeve fixedly attached to the needle body, wherein the sleeve is fitted over an exterior surface of the needle body, and wherein the sleeve has a distal sleeve end that covers only a proximal portion of the delivery opening such that a portion of the delivery opening is not covered by the sleeve, wherein the delivery opening extends underneath the distal sleeve end towards the proximal end of the needle body.

The delivery needle apparatus described in the preceding paragraph may, in various embodiments, include one or more of the following features: the needle wall that extends into the insertion section may be parallel with the longitudinal axis; the needle wall extending into the insertion section may follow a curved path relative to the longitudinal axis; the sleeve may extend proximally from the delivery opening to the proximal end of the needle body; the sleeve may have a proximal end located between the proximal end of the needle body and the delivery opening; the sleeve may include polymeric material; the sleeve may consist essentially of polymeric material; the needle body may have a metallic needle wall; etc.

In another aspect, the present invention may provide a method of manufacturing a delivery needle apparatus by providing a delivery needle includes a needle body that extends along a longitudinal axis from a proximal end to an insertion section, wherein the needle body has a needle wall defining a lumen that extends into the insertion section and a delivery opening within an insertion section. The method may further include fixedly attaching a sleeve to the needle body, wherein the sleeve is fitted over an exterior surface of the delivery needle body, and wherein at least a portion of the delivery opening is contained within the sleeve.

In some embodiments, the delivery needle apparatus used in the methods may include a delivery opening that is formed through the needle wall within the insertion section, wherein the delivery opening has a longitudinal length measured along the longitudinal axis. Further, only a proximal portion of the delivery opening may be located within the sleeve such that a portion of the delivery opening is not contained within the sleeve, and wherein the delivery opening extends towards the proximal end of the needle body within the sleeve.

In other embodiments, the delivery opening of the delivery needle body used in the methods may be located entirely within the sleeve such that an extension portion of the sleeve extends past the insertion section of the delivery needle body.

The extension portion of the sleeve may be curved relative to the longitudinal axis of the delivery needle body.

In various embodiments, the methods of the present invention may include one or more of the following features: fixedly attaching the sleeve may include locating the sleeve over the needle body followed by reducing an inner diameter of the sleeve; fixedly attaching the sleeve may include adhesively attaching the sleeve to the needle body; etc.

The above summary is not intended to describe each embodiment or every implementation of the present invention. Rather, a more complete understanding of the invention will become apparent and appreciated by reference to the following Detailed Description of Exemplary Embodiments and claims in view of the accompanying figures of the drawing.

BRIEF DESCRIPTIONS OF THE FIGURES OF THE DRAWING

The present invention will be further described with reference to the figures of the drawing.

FIG. 1 is a side view of a delivery needle apparatus in accordance with one embodiment of the present invention.

FIG. 2 is an enlarged cross-sectional view of the insertion section of the delivery needle apparatus of FIG. 1.

DETAILED DESCRIPTION OF ILLUSTRATIVE EMBODIMENTS

Figure 3:
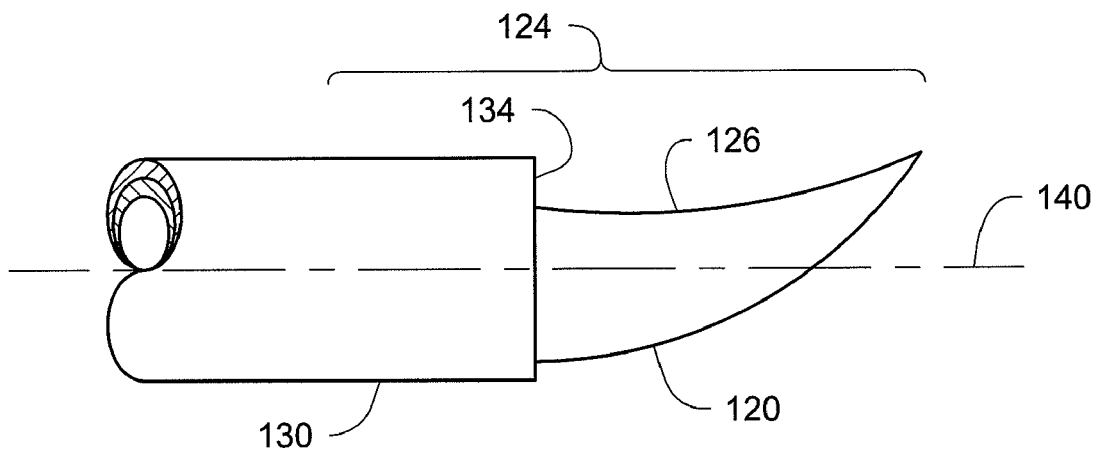
FIG. 3 is an enlarged side view of an insertion section of a delivery needle apparatus in accordance with another embodiment of the present invention.

In the following detailed description of illustrative embodiments of the invention, reference is made to the accompanying figures of the drawing which form a part hereof, and in which are shown, by way of illustration, specific embodiments in which the invention may be practiced. It is to be understood that other embodiments may be utilized and structural changes may be made without departing from the scope of the present invention.

As used herein, "a," "an," "the," "at least one," and "one or more" are used interchangeably. The term "and/or" (if used) means one or all of the listed elements or a combination of any two or more of the listed elements.

FIG. 1 is a side view of a delivery needle apparatus 10 in accordance with one embodiment of the present invention and FIG. 2 is an enlarged cross-sectional view of the distal end of the delivery needle apparatus of FIG. 1 (which includes the insertion section as described herein). The delivery needle apparatus 10 may include a hub 12, delivery needle body 20, and a sleeve 30. Delivery needle apparatus 10 of the present invention may be used to deliver any suitable elongate medical devices including, but not limited to, catheters, leads, guidewires, etc.

The proximal end 22 of the needle body 20 is adjacent and attached to the hub 12. A clinician (e.g., surgeon) may use the hub 12 to hold, move, and/or manipulate the delivery needle apparatus 10 during use. Generally, the hub 12 may have a plurality of sides, a length, and a diameter that allows manipulation of the hub 12 between, e.g., the thumb and forefinger.

The delivery needle body 20 includes an insertion section 24 (i.e., the distal end) and a lumen 21 (i.e., a hollow bore) that extends from the proximal end 22 of the needle body 20 to the insertion section 24. The lumen 21 is defined by a wall 23 of the needle body 20. A delivery opening 26 is located in the insertion section 24 and the delivery opening 26 is in fluid communication with the lumen 21.

The insertion section 24 may terminate in a sharp tip 28 as depicted in FIGS. 1 & 2 that is suited for penetrating tissue such as, e.g., skin, dura mater, etc. The delivery needle body 20 is defined by a delivery opening 26 proximate the insertion section 24 and another opening (not shown) at the proximal end 22.

Use of the delivery needle body 20 typically involves insertion of an elongate medical device into the lumen 21 through an opening at the proximal end 22 of the needle body 20. The opening at the proximal end 22 provides access to the lumen 21 which, as described herein, extends through the delivery needle body 20 to the insertion section 24.

The insertion section 24 includes a delivery opening 26 through which the elongate medical device can exit from the delivery needle apparatus 10 for positioning at a selected internal body location. In other words, the delivery opening 26 is in fluid communication with the opening at the proximal end 22 through the lumen 21 that extends through the delivery needle body 20. An elongate medical device is typically delivered through the delivery opening 26 after the insertion section 24 of the needle body 20 is positioned at a selected location of the patient for the particular procedure being performed.

The delivery opening 26 may be formed such that the edge of the delivery opening 26 forms an angle relative to the longitudinal axis 40 that extends from the proximal end 22 of the needle body 20 to the distal end of the needle body 20 (which includes the insertion section 24). For example, the delivery opening 26 may be beveled at an angle α (alpha) of about 30 degrees relative to axis 40 (as depicted in FIG. 2). Delivery opening 26 may alternatively be beveled at any other suitable angle relative to the axis 40.

The delivery needle body 20 may have any cross-sectional shape (e.g., circular, oval, rectangular, octagonal, elliptical, etc.) to facilitate its use with many different elongate medical devices of different shapes and sizes. Although the outer cross-sectional shape and the cross-sectional shape of the lumen 21 formed through the needle body may be the same (e.g., both the outer surface of the needle body 20 and the lumen 21 may be circular), they may also be different (e.g., the outer surface of the needle body 20 may be octagonal and the lumen 21 may be circular). Also, the delivery needle body 20 may have any suitable length (e.g., for a larger patient or a difficult paramedian approach) and/or width depending on the application.

Further, the cross section and width/diameter may not be uniform throughout the length of the delivery needle body 20. For example, the outer surface of the delivery needle body 20 may be tapered and the lumen located therein may also be tapered. Alternatively, the outer surface of the delivery needle 20 may be tapered while the lumen extending through the needle body 20 may have a uniform cross-sectional size from the proximal end to the distal end of the needle body 20. In such a design, the thickness of the wall 23 forming the needle body 20 may change over the length of the needle body 20 (wherein the wall thickness is measured perpendicular to the longitudinal axis 40).

The wall 23 of the delivery needle body 20 may be substantially parallel to the longitudinal axis 40 (as seen in FIG. 1). Alternatively, the wall 23 forming the delivery needle body 20 may not be substantially parallel to the longitudinal axis 40. For example, the wall 23 of the delivery needle body 20 may curve relative to the longitudinal axis 40 near the insertion section 24 relative to the axis 40 to facilitate and guide the elongate medical device in a particular direction as it exits the needle body 20 through the delivery opening 26.

The delivery needle body 20 may, for example, have a circular cross section with a diameter of about 1 millimeter (mm) to about 4 mm and a length of about 5 centimeters (cm) to about 15 cm. The wall 23 of the delivery needle body 20 may be about 0.1 mm to about 0.5 mm thick. These and all other dimensions provided in connection with the invention are presented as examples of potentially suitable dimensions, although devices and apparatus constructed with dimensions outside of the presented exemplary ranges may still fall within the scope of the present invention.

The delivery needle body 20 may be formed of any medically acceptable metal or material, such as stainless steel, titanium, etc. The interior of the wall 23 of the delivery needle body 20 may include a slippery, nonstick material to provide ease of insertion and withdrawal of elongate medical devices.

Although not shown, the delivery needle apparatus 10 may include stylet that may be inserted into the lumen 21 of the delivery needle body 20. The stylet may be used to obstruct and/or seal the delivery opening 26 (to, e.g., prevent coring of tissue), increase rigidity of the delivery needle body 20, etc. On example of one potentially suitable stylet may be described in, e.g., U.S. Pat. No. 5,669,882 (Pyles).

As depicted in FIGS. 1 & 2, the delivery needle apparatus 10 includes a sleeve 30 fixedly attached to the exterior surface of the delivery needle body 20. The sleeve 30 may be formed of any medically acceptable material, such as, but not limited to, a polymeric material, metallic material, etc. The wall of the sleeve 30 may have any suitable thickness, e.g., the wall thickness (measured perpendicular to the longitudinal axis 40) may be about 0.1 mm to about 0.5 mm thick.

As used herein, "fixedly attached" means that the sleeve 30 is attached to the needle body 20 in a manner that prevents movement of the sleeve 30 relative to the needle body 20 during use of the delivery needle apparatus 10. The sleeve 30 may be fixedly attached to the exterior surface of the delivery needle body 20 by, e.g., friction between the inner surface of the sleeve 30 and the exterior surface of the needle body 20. The friction may be developed by any suitable technique, for example, the sleeve 30 may be made of a shrink-fit polymeric material that is located over the exterior surface of the needle body 20 and then heated or otherwise processed such that the internal diameter of the sleeve 30 is reduced. In another embodiment, the sleeve 30 may be fitted over the needle body in the presence of a lubricant, solvent, etc. and, after removal of the lubricant, solvent, etc., the sleeve 30 may be fixedly attached to the exterior surface of the needle body 20. In still another alternative, adhesive may be used to attach the sleeve 30 to the exterior surface of the needle body 20. Other alternatives may for frictionally attaching a sleeve 30 to the exterior of the needle body 20 may also be used.

The sleeve 30 extends from a proximal end 32 to a distal end 34. The proximal end 32 of the sleeve 30 may correspond to the proximal end 22 of the delivery needle body 20 as depicted in FIG. 1 and the distal end 34 of the sleeve 30 may be located within the insertion section 24 of the delivery needle body 20. In some embodiments, however, sleeve 30 may not extend to the proximal end 22 of the delivery needle body 20. For example, the proximal end 32 of the sleeve 30 may be located between the proximal end 22 of the delivery needle body 20 and the delivery opening 26.

The relationship between the sleeve 30 and the insertion section 24 and delivery opening 26 of the delivery needle body 20 may be characterized, in some embodiments, as an apparatus in which at least a portion of the delivery opening 26 is contained within the sleeve 30. As used herein, the phrase "contained within" means that at least a portion of the delivery opening 26 can only be accessed by passing through the distal end of the sleeve 30. In other words, the sidewalls of the sleeve 30 surround at least a portion of the delivery opening 26 when moving radially away from the longitudinal axis 40.

In some embodiments, the delivery opening 26 may be described as being formed through the needle wall within the insertion section 24, with the delivery opening 26 having a longitudinal length measured along the longitudinal axis 40. In the embodiment depicted in FIGS. 1 & 2, only a proximal portion of the delivery opening 26 is contained within the sleeve 30 such that a portion of the delivery opening 26 is not contained within the sleeve 30. The proximal portion of the delivery opening 26 extends towards the proximal end of the needle body 20 within the sleeve 30.

The distal end 34 of the sleeve 30 extends to cover only a proximal portion of the delivery opening 26 such that at least the trailing edge 25 of the delivery opening 26 is covered by the sleeve 30 (where the trailing edge 25 is the portion of the edge of the delivery opening 26 that is closest to the proximal end 22 of the delivery needle body 20). At least in one embodiment, the distal sleeve end 34 may extend over the delivery opening 26 to about 10 millimeters or less from the tip 28 of the delivery needle body 20. In other embodiments, the distal end 34 covers about 50% or less of the length of the edge that defines the delivery opening 26 in the needle body 20. The relationship between the distal end 34 of the sleeve 30 and the delivery opening may alternatively be characterized in terms of overhang, where the distal sleeve end 34 may extend about 5 mm or less over the trailing edge 25 of the proximal portion of the delivery opening 26.

As discussed herein, the distal end of the sleeve 30 is positioned to cover at least the trailing edge 25 of the delivery opening 26. FIG. 2 depicts the trailing edge 25 covered by the sleeve 30 because the distal end 34 of the sleeve 30 is located between the trailing edge 25 of the opening 26 and the tip 28 of the needle body 20.

Figure 5:
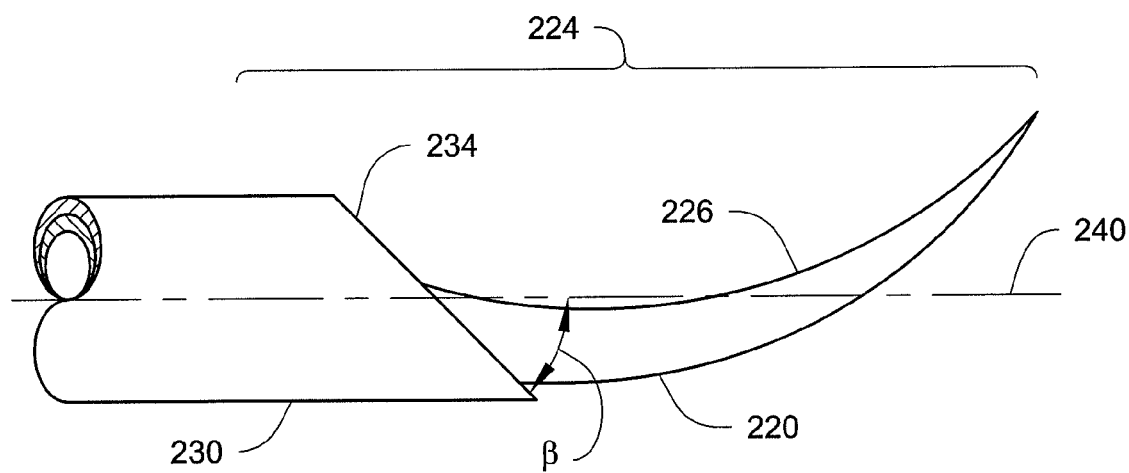
FIG. 5 is an enlarged side view of an insertion section of a delivery needle apparatus in accordance with yet another embodiment of the present invention.
Figure 6:
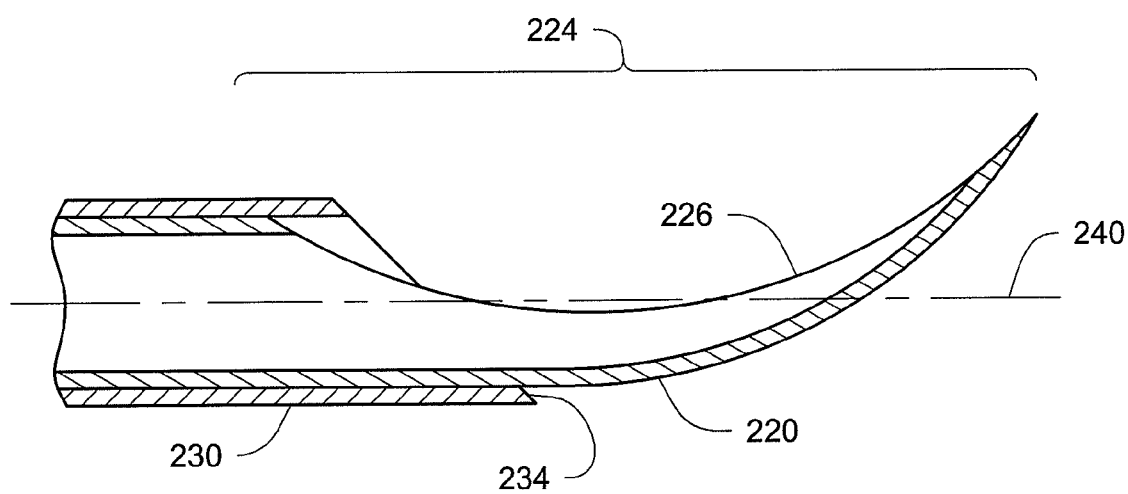
FIG. 6 is an enlarged cross-sectional view of the insertion section of the delivery needle apparatus of FIG. 5.

The distal end 34 of the sleeve 30 may form an edge located in a plane that is perpendicular to the axis 40 as depicted in, e.g., FIGS. 1 & 2. However, the distal end 34 of the sleeve 30 may alternatively form an edge located in a plane that is not perpendicular to the axis 40. For example, the distal end 34 of the sleeve 30 could be beveled or take any other selected shape provided that the trailing edge 25 of the delivery opening 26 is covered by the sleeve 30. FIGS. 5 & 6, described in further detail herein, depict embodiments in which the distal end of the sleeve is beveled.

The sleeve 30 may assist in aligning an elongate medical device during movement of the device through the delivery opening 26 of the needle body 20. The sleeve 30 may align the elongate medical device so that it is restricted from engaging the edge of the delivery opening 26 located under the sleeve 30.

For example, a catheter delivered through the delivery needle body 20 may not be straight (i.e., the catheter may be curved when unrestrained). While this curved catheter is being delivered through the delivery needle body 20, the catheter will conform to the lumen 21 of the delivery needle body 20 (i.e., the catheter "straightens"). However, upon exiting the delivery needle body 20, the curved catheter may resume its curved form, which, in turn, may cause the catheter to bend towards the trailing edge 25 of the delivery opening 26. However, the portion of the distal end 34 of sleeve 30 that extends over the trailing edge of the delivery opening 26 may restrain the catheter from bending.

Also, for example, a curved catheter may be withdrawn into the lumen 21 of the needle body 20. In such an instance, the sleeve 30 may "straighten" the catheter as it is being withdrawn.

The sleeve 30 may protect straight elongate medical devices as well. For example, straight elongate medical devices may become twisted or misaligned during delivery due to various reasons. The sleeve 30 may guide or align the elongate medical devices as they enter the delivery opening 26.

The insertion section 24 of the delivery needle body 20 and the distal end 34 of the sleeve 30 may have different, alternative configurations. FIGS. 3-6 illustrate two such alternative configurations.

FIG. 3 is a side view of an insertion section of a delivery needle apparatus in accordance with another embodiment of the present invention. In this embodiment, the insertion portion 124 of the delivery needle body 120 is curved relative to the longitudinal axis 140. The insertion portion 124 may be curved to, e.g., facilitate and guide the elongate medical device in a selected direction as the device exits the delivery needle 120.

Figure 4:
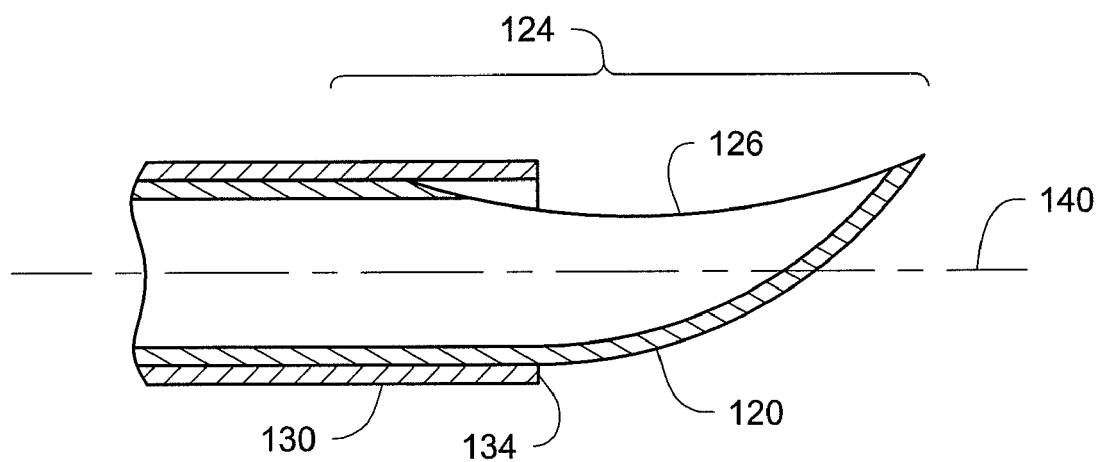
FIG. 4 is an enlarged cross-sectional view of the insertion section of the delivery needle apparatus of FIG. 3.

FIG. 4 is an enlarged cross-sectional view of the insertion section of the delivery needle apparatus of FIG. 3. In this view, the relationship between the delivery opening 126 of the delivery needle body 120 and the distal end 134 of the sleeve 130 is more clearly shown. Similar to the embodiment depicted in FIG. 2, a portion of the sleeve 130 covers only a portion of the delivery opening 126 such that a portion of the delivery opening 126 is not covered by the sleeve 130. As a result, the delivery opening 126 may be characterized as extending underneath the sleeve 130 towards the proximal end of the needle body 120 such that the trailing edge of the delivery opening 126 is covered by the sleeve 130. In another characterization, the delivery needle apparatus of FIGS. 3 & 4 may be described as one in which at least a portion of the delivery opening 126 is contained within the sleeve 130.

FIG. 5 is side view of an insertion section of a delivery needle apparatus in accordance with yet another embodiment of the present invention. In this embodiment, the insertion portion 224 of the delivery needle body 220 is curved similar to the insertion portion 124 of the embodiment in FIG. 3. However, in this embodiment, the distal end 234 of sleeve 230 forms an edge that is not located in a plane that is perpendicular to the axis 240. Instead, the distal end 234 of sleeve 230 forms an edge that is beveled at an angle β (beta).

FIG. 6 is an enlarged cross-sectional view of the insertion section of the delivery needle apparatus of FIG. 5. In this view, the delivery opening 226 of the delivery needle body 220 and the distal end 234 of the sleeve 230 are more clearly shown. Similar to the embodiments depicted in FIG. 2 and FIG. 4, a portion of the sleeve 230 covers only a portion of the delivery opening 226 such that a portion of the delivery opening 226 is not covered by the sleeve 230. As a result, the delivery opening 226 may be characterized as extending underneath the sleeve 230 towards the proximal end of the needle body 220 such that the trailing edge of the delivery opening 226 is covered by the sleeve 230. In another characterization, the delivery needle apparatus of FIGS. 5 & 6 may be described as one in which at least a portion of the delivery opening 226 is contained within the sleeve 230.

Figure 7:
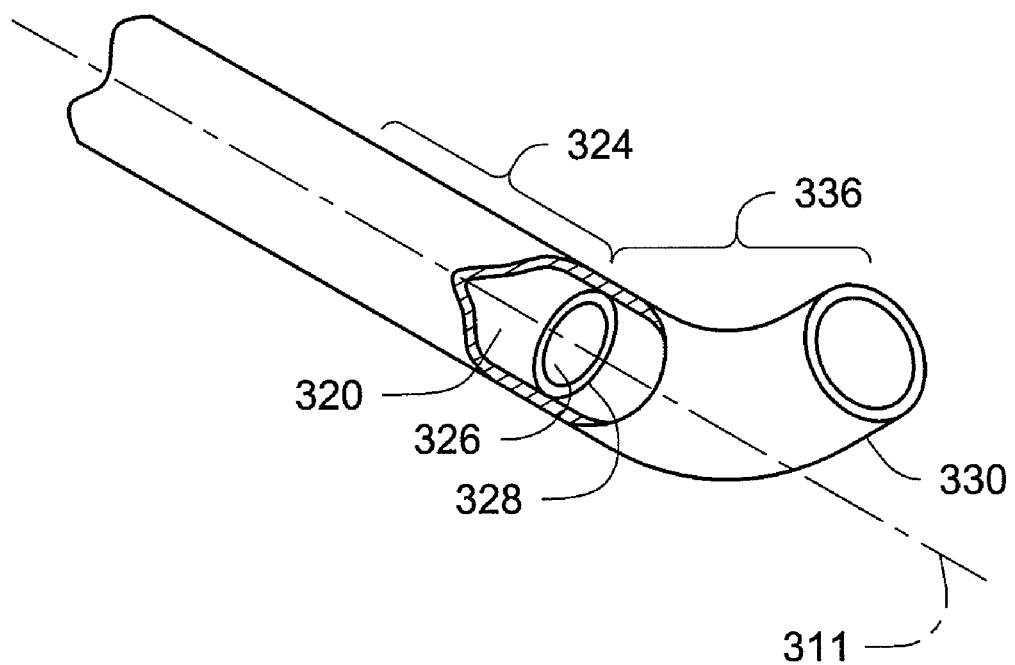
FIG. 7 is a perspective view of a portion of another exemplary delivery needle apparatus.

FIG. 7 depicts another embodiment of a delivery needle apparatus including a delivery needle body 320 and a sleeve 330. A portion of the sleeve 330 proximate the delivery end opening 326 of the delivery needle body 320 has been removed to reveal the features within the sleeve 330. The delivery needle body 320 includes a delivery opening 326 that is entirely contained within the sleeve 330 such that an extension portion 336 of the sleeve 330 extends past the insertion section 324 of the delivery needle body 320. The extension portion 336 may extend past the distal end 328 of the delivery needle body 320 by any selected length, e.g., 25 mm or less, etc.

In the depicted embodiment, the delivery opening 326 in the delivery needle body 320 is formed along a plane that is perpendicular to the longitudinal axis 311 of the delivery needle body 320, although such an arrangement is not required.

An extension portion 336 of the sleeve 330 of the embodiment depicted in FIG. 7 extends past the distal end 328 of the delivery needle body 320 curves relative to the longitudinal axis 311. Curvature of the extension portion 336 of the sleeve 330 may be used to, e.g., guide an elongate medical device in a direction that is not aligned with the longitudinal axis 311.

The amount of curvature in the extension portion 336 of the sleeve may, in some embodiments, be adjustable. The adjustment may be may be made using any suitable technique or combination of techniques such as, e.g., manipulation resulting in permanent deformation of the sleeve, trimming of an existing curved sleeve 330 (where, e.g., trimming the sleeve reduces the angle at which an elongate medical device exits the sleeve 330 relative to the longitudinal axis 311), etc.

Another optional feature is that the sleeve 330 (or at least the extension portion 336) may be made of a shape memory material (e.g., shape memory metal, shape memory polymer, etc.) that may be provided in a straight configuration, but which transforms to a curved configuration when, e.g., heated during use (by body heat, etc.).

The complete disclosure of the patents, patent documents, and publications cited in the Background, the Detailed Description of Exemplary Embodiments, and elsewhere herein are incorporated by reference in their entirety as if each were individually incorporated.

Illustrative embodiments of this invention are discussed and reference has been made to possible variations within the scope of this invention. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

The invention claimed is:
1. A delivery needle apparatus comprising:
a delivery needle body extending along a longitudinal axis from a proximal end to an insertion section, wherein the delivery needle body comprises a needle wall defining a lumen that extends into the insertion section, and wherein the delivery needle body further comprises a delivery opening located within the insertion section, wherein the delivery opening is in fluid communication with the lumen; and
a sleeve fixedly attached to the delivery needle body by friction between an inner surface of the sleeve and an exterior surface of the needle body, wherein at least a portion of the delivery opening is contained within the sleeve, wherein the fixedly attached sleeve is attached to the needle body in a manner that prevents movement of the sleeve relative to the needle body during use of the delivery needle apparatus.

2. A delivery needle apparatus according to claim 1, wherein the delivery opening is formed through the needle wall within the insertion section, wherein the delivery opening comprises a longitudinal length measured along the longitudinal axis.

3. A delivery needle apparatus according to claim 2, wherein only a proximal portion of the delivery opening is located within the sleeve such that a portion of the delivery opening is not contained within the sleeve, and wherein the delivery opening extends towards the proximal end of the needle body within the sleeve.

4. A delivery needle apparatus according to claim 1, wherein the sleeve extends proximally from the delivery opening to the proximal end of the needle body.

5. A delivery needle apparatus according to claim 1, wherein the sleeve comprises a proximal end located between the proximal end of the needle body and the delivery opening.

6. A delivery needle apparatus according to claim 1, wherein the sleeve consists essentially of polymeric material.

7. A delivery needle apparatus according to claim 1, wherein the needle body comprises a metallic needle wall.

8. A delivery needle apparatus comprising:
   a needle body extending along a longitudinal axis from a proximal end to an insertion section, wherein the needle body comprises a needle wall defining a lumen that extends into the insertion section;
   a delivery opening formed through the needle wall within the insertion section, wherein the opening comprises a longitudinal length measured along the longitudinal axis, and wherein the opening is in fluid communication with the lumen; and
   a sleeve fixedly attached to the needle body, wherein the sleeve is fitted over an exterior surface of the needle body, and wherein the sleeve comprises a distal sleeve end that covers only a proximal portion of the delivery opening such that a portion of the delivery opening is not covered by the sleeve, wherein the delivery opening extends underneath the distal sleeve end towards the proximal end of the needle body, and wherein the fixedly attached sleeve is attached to the needle body in a manner that prevents movement of the sleeve relative to the needle body during use of the delivery needle apparatus.

9. A delivery needle apparatus according to claim 8, wherein the needle wall defining a lumen that extends into the insertion section is parallel with the longitudinal axis.

10. A delivery needle apparatus according to claim 8, wherein the needle wall extending into the insertion section follows a curved path relative to the longitudinal axis.

11. A delivery needle apparatus according to claim 8, wherein the sleeve extends proximally from the delivery opening to the proximal end of the needle body.

12. A delivery needle apparatus according to claim 8, wherein the sleeve comprises a proximal end located between the proximal end of the needle body and the delivery opening.

13. A delivery needle apparatus according to claim 8, wherein the sleeve consists essentially of polymeric material.

14. A delivery needle apparatus according to claim 8, wherein the needle body comprises a metallic needle wall.

15. A delivery needle apparatus comprising:
   a delivery needle body extending along a longitudinal axis from a proximal end to an insertion section, wherein the delivery needle body comprises a needle wall defining a lumen that extends into the insertion section, and wherein the delivery needle body further comprises a delivery opening located within the insertion section, wherein the delivery opening is in fluid communication with the lumen; and
   a sleeve fixedly attached to the delivery needle body by adhesive located between an inner surface of the sleeve and an exterior surface of the needle body, wherein at least a portion of the delivery opening is contained within the sleeve.

16. A delivery needle apparatus according to claim 15, wherein the delivery opening is formed through the needle wall within the insertion section, wherein the delivery opening comprises a longitudinal length measured along the longitudinal axis.

17. A delivery needle apparatus according to claim 16, wherein only a proximal portion of the delivery opening is located within the sleeve such that a portion of the delivery opening is not contained within the sleeve, and wherein the delivery opening extends towards the proximal end of the needle body within the sleeve.

18. A delivery needle apparatus according to claim 15, wherein the delivery opening of the delivery needle body is located entirely within the sleeve such that an extension portion of the sleeve extends past the insertion section of the delivery needle body.

19. A delivery needle apparatus according to claim 18, wherein the extension portion of the sleeve is curved relative to the longitudinal axis of the delivery needle body.

20. A delivery needle apparatus according to claim 15, wherein the sleeve extends proximally from the delivery opening to the proximal end of the needle body.

21. A delivery needle apparatus according to claim 15, wherein the sleeve comprises a proximal end located between the proximal end of the needle body and the delivery opening.

* * * * *